| United States Patent [19] | [11] 3,957,982 |
|---|---|
| Lachnit-Fixson et al. | [45] May 18, 1976 |

[54] METHOD FOR CONTRACEPTION BY THE APPLICATION OF COMBINATION-TYPE SEQUENTIAL PREPARATIONS

[75] Inventors: Ursula Lachnit-Fixson, Berlin, Germany; Alan G. Pitchford, High Hurstwood, near Uckfield, England

[73] Assignee: Schering Aktiengesellschaft, Berlin & Bergkamen, Germany

[22] Filed: Dec. 23, 1974

[21] Appl. No.: 535,575

[30] Foreign Application Priority Data
Dec. 21, 1973 Germany............................ 2365103

[52] U.S. Cl.................................. 424/238; 424/239
[51] Int. Cl.².......................................... A61K 31/56
[58] Field of Search............................ 424/238, 239

[56] References Cited
UNITED STATES PATENTS

| 3,502,772 | 3/1970 | Ijzerman | 424/239 |
|---|---|---|---|
| 3,568,828 | 3/1971 | Lerner | 424/239 |
| 3,639,600 | 2/1972 | Hendrix | 424/243 |
| 3,733,407 | 5/1973 | Segre | 424/239 |
| 3,795,734 | 3/1974 | Rochefort | 424/238 |

Primary Examiner—Elbert L. Roberts
Attorney, Agent, or Firm—Millen, Raptes & White

[57] ABSTRACT

Method of contraception in which an estrogen and a progestagen are orally administered daily for 21 days, the first 4–6 days at a low contraceptively effective daily dose, the next 4–6 days at a daily estrogen dose 1–2 times and a daily progestrogen dose 1–1.5 times that of the first 4–6 days, and for the next 9–11 days at a daily estrogen dose from that of the first 4–6 days to that of the next 4–6 days and a daily progestogen dose higher than either prior daily dose, up to 3 times that of the initial dose, followed by 7 days without hormone administration.

20 Claims, No Drawings

METHOD FOR CONTRACEPTION BY THE APPLICATION OF COMBINATION-TYPE SEQUENTIAL PREPARATIONS

BACKGROUND OF THE INVENTION

Numerous hormonal methods for contraception are known, i.e., the oral administration of combination-type preparations, e.g., "Ovulen", "Anovlar", "Lyndiol" and similar combinations of estrogenic and gestagenic active agents. Also conventional is the administration of purely sequential preparations, such as, for example, "Ovanone", etc., wherein first an estrogen is administered at a high dosage in the absence of gestagen, over a period of 7 days, and thereafter the estrogen is administered at the same high dosage in combination with a relatively high amount of gestagen over a period of 15 days, with the next 6 days being a blank period without administration of estrogenic or gestagenic agent in order to mimic the normal 28-day menstrual cycle of the woman.

The administration of modified sequential preparations is likewise conventional, such as, for example, "Kombiquens", "Tri-Ervonum" and "Oraconal", etc., wherein first an estrogen is administered at a high dosage in combination with a low amount of gestagen over a period of 16 days, and subsequently the estrogen is administered over a period of about 7 days at the same high dosage in combination with an amount of gestagen about 5–10 times the original amount. See U.S. Pat. No. 3,568,828. To adapt to the natural 28-day cycle of the female, a five-day hormone-free period follows the administration of these preparations wherein placebos or any desired other non-contraceptive effective agents are taken, such as, for example, tonics, iron supplements, etc.

It is also known to administer two-stage combination-type oral contraceptives, with a combination of an estrogen at a low dosage and a progestogen at a low dosage first being administered for 10–12 days and subsequently a combination of the same dosage of estrogen and a dosage of progestogen increased to 2–3 times as much, is ingested for 11–9 days. To adapt to the normal about 28-day female cycle, a 5–7 day hormone-free period follows in which no estrogens or progestogens are ingested. For continuity of dosage, a placebo or a nonhormonal effective agent is usually administered during this period. See application Ser. No. 350,590, filed Apr. 12, 1973.

Disadvantages inherent in the administration of the aforementioned pure and modified sequential products involving the administration of relatively high doses of estrogen, are, in addition to the usual symptoms due to excessive estrogen, e.g., gastrointestinal disturbances, nausea, weight gain with formation of edema, etc., an increase in the risk of thromboembolic disease. These disadvantages would be avoided by the administration of the above-described two-stage combination contraceptives, but in the latter it is desirable to improve the compatibility and/or the control of the cycle.

In application Ser. No. 486,757, filed July 9, 1974, there is claimed a contraceptive method in which a low but contraceptively effective daily dosage of an estrogen and a progestogen are administered for 10–12 days and thereafter a combination of an estrogen and a progestogen are administered at slightly higher dosages.

SUMMARY OF THE INVENTION

According to this invention, reliable contraception is achieved by administering for 21 successive days to a female of child-bearing age a combination of an estrogen and a progestogen, for the first 4–6 days in a low but contraceptively effective daily dosage; for the next 4–6 days, at an estrogen daily dosage from 1–2 times the initial daily low dosage and at a progestogen daily dosage of from 1 – 1.5 times the dosage of the first 4–6 days; and for the next 9–11 days, at a daily estrogen dosage of from the initial daily dosage to the subsequent daily dosage and at a progestogen daily dosage higher than the previous daily dosages of up to 3 times that of the first daily dosage, followed by 7 days without progestogen and estrogen administration.

The total number of days during which the progestogen and estrogen combinations are administered daily is 21. These are followed by 7 days free of hormone administration to approximate the natural 28-day menstrual cycle.

In a composition aspect, this invention relates to a three-stage or a contraceptive composition comprising 21 separate dosage units, adapted for successive daily oral ingestion, consisting essentially of:

as the first stage, 4–6 dosage units containing, in admixture with a pharmaceutically acceptable carrier, a combination of an estrogen and a progestogen at low but contraceptively effective respective dosages, followed by, as the second stage, 4–6 dosage units containing, in admixture with a pharmaceutically acceptable carrier, a combination of an estrogen at a dosage from the same to twice the dosage of the first stage, and a progestogen at a dosage from 1 – 1.5 times the dosage of the first stage, followed by, as the third stage, 9–11 dosage units containing, in admixture with a pharmaceutically acceptable carrier, a combination of an estrogen at a dosage from that of the first stage to that of the second stage, and a progestogen at a higher dosage than the first and second stages up to three times that of the first stage, optionally followed by, as the fourth stage, 7 dosage units free of estrogen and progestogen.

DETAILED DISCUSSION

The "low but contraceptively effective dosage" employed in the first stage means a dosage significantly lower, e.g., 60 to 20%, preferably 50 to 30%, of the contraceptive dose conventionally employed with a combination of the selected estrogen and progestogen when administered conventionally in a non-sequential manner. As will be apparent, the weight amount of the dosage at each dosage level will depend upon the estrogenic and progestogenic activity, respectively, of the selected components of the dosage units.

Suitable as the estrogen component for the contraceptive method of this invention are the conventional estrogens. The selected estrogen should be administered in a daily dosage in the first 4–6 days equal in contraceptive activity to that of 0.020 – 0.050 mg. daily of 17α-ethinylestradiol. The amount of estrogen administered daily in the 4–6 days of the second phase should be equal in contraceptive activity to a daily dosage of about 0.030 – 0.050 mg. of 17α-ethinylestradiol, i.e., 1 – 1.5 times the first dosage level. The amount of estrogen administered daily during the 9–11 days of the third phase should be equal in contraceptive activity to a daily dosage of about 0.025 – 0.050 mg. of 17α-ethinylestradiol.

In addition to 17α-ethinylestradiol, esters and ethers of 17α-ethinylestradiol are also suitable as the estrogen component. Also suitable are, e.g., the natural estrogens, e.g., estrone, estradiol and estriol, and their esters, e.g., estradiol valerate, as well as the synthetic estrogens. 17α-Ethinylestradiol is preferred.

As the progestogen component of this invention, all progestationally active compounds are suitable. The progestogen preferably is administered in a daily dosage in the first 4–6 days corresponding in progestogenic activity to 0.040 – 0.090 mg. of d-norgestrel per day. The amount of progestogen administered daily in the 4–6 days of the second phase should be equivalent in progestogenic activity to the daily administration of 0.050 – 0.125 mg. of d-norgestrel. The amount of progestogen administered daily during the 9–11 days of the third phase should be equal in progestogenic activity to the daily administration of about 0.100 – 0.250 mg. of d-norgestrel.

Suitable as the progestogen component are, e.g., progesterone and its derivatives, e.g., 17-hydroxyprogesterone esters and 19-nor-17-hydroxyprogesterone esters, 17α-ethinyltestosterone, as well as 17α-ethinyl-19-nortestosterone and the derivatives thereof. The term "derivatives" as used herein means compounds which are formed by the introduction of an additional double bond or double bonds, by substitution or by the production of a functional derivative, e.g., esters, ethers, ketals, etc.

Such additional double bonds can be present, inter alia, in the 1(2)-, 6(7)- and/or 16(17)-position. Suitable substituents are, among others, halogen, particularly fluorine, chlorine and bromine atoms, lower alkyl, especially the methyl group, alkenyl, alkinyl, especially the ethinyl group, and/or the hydroxy group, each of which can be in the 4-, 6-, 7-, 16- and/or 17-position, as well as methylene groups which can be in the 1(2)-, 6(7)- 15(16)- and/or 16(17)-position. Suitable esters are the esters of acids customarily employed in the steroid chemistry for the esterification of the steroid hydroxy groups, e.g., hydrocarbon carboxylic acids, especially alkanecarboxylic acids, of 1–11 carbon atoms, more preferably 2–5 carbon atoms. Examples of ethers are alkyl, e.g., of 1–11 carbon atoms, benzyl and tetrahydropyranyl ethers. Examples of ketals are those of α,β-, α,γ - and β, γ -alkanediols, e.g., of 1–8 carbon atoms, especially ethanediol and the propanediols.

Preferred progestogens are d-norgestrel, 17α-ethinyl-19-nortestosterone acetate, and cyproterone acetate.

The combination of progestogen and estrogen can be the same or also different in the first and second or third stages. If a different progestogen and/or estrogen is utilized in the first, second and/or third stages, the present invention has the additional advantage above and beyond the aforedescribed advantages in that the side effects of a specific progestogen (or estrogen) are reduced or eliminated, in that such progestogen (or estrogen) is administered in one or two stages only while in the other stage or stages, another progestogen (or estrogen) having a competitive array of side effects is administered.

Thus, it is possible, for example, to utilize in one stage the estrogen in combination with a progestogen derived from testosterone or 19-nortestosterone and having in the 17α-position, optionally a substituted hydrocarbon group. These (19-nor-) testosterone derivatives generally exhibit a low androgenic side effect. In one of the other stages, the estrogen can then be used in combination with a progestogen derived from progesterone which lacks the androgenic side effect inherent in the testosterone or 19-nortestosterone compounds. Particularly advantageous progestogens are those possessing an antiandrogenic side effect in addition to the progestational activity.

It is also possible, for example, to employ, in one stage, a progestogen in combination with an estrogen derived from 17α-ethinylestradiol. These estrogens generally have a lessor gastric compatibility and exert a stronger effect on carbohydrate and fat metabolism. In one of the other stages, the progestogen can then be utilized in combination with an estrogen derived from a natural estrogen lacking the above-described side-effects.

If, in the first, second and/or third stages, different progestogens are utilized, it is preferred to employ in the first and second stages, a progestogen which is a testosterone or 19-nortestosterone derivative and; in the third stage, a progestogen which is a progesterone derivative.

If, in the first and second or third stages, different estrogens are used, the preferred embodiment is to employ, in the first and second stages, an estrogen which is a 17α-ethinylestradiol derivative and, in the third stage, an estrogen which lacks a 17α-ethinyl group.

The estrogenic and progestational effective agent components are preferably administered together orally, but they can also be administered separately or parenterally. For this purpose, the effective agents are processed, together with the usual additives, vehicles and/or flavor-ameliorating agents employed in galenic pharmacy, in accordance with known methods. For the preferred oral administration, especially suitable are tablets, dragees, capsules, pills, suspensions or solutions, and for parenteral application especially oily solutions, such as, for example, sesame oil or castor oil solutions which can optionally additionally contain a diluent, e.g., benzyl benzoate or benzyl alcohol.

For the preferred oral application, the three-stage combination-type contraceptives are preferably packaged in the form of a pharmaceutical kit in which the daily dosages are arranged for proper sequential ingestion.

Accordingly, this invention also relates to pharmaceutical packs which contain combination-type contraceptives in 28 dosage units in a synchronized, fixed sequence, wherein the sequence or arrangement of the dosage units corresponds to the stages of daily administration.

The pharmaceutical pack can be, e.g., in the form of a see-through package with 28 dosage units arranged sequentially and consisting of 6 dragees for the first stage, followed by 5 dragees for the second stage, followed by 10 dragees for the third stage, and followed by 7 placebos, one dragee to be taken daily over a period of 28 days.

Without further elaboration, it is believed that one skilled in the art can, using the preceding description, utilize the present invention to its fullest extent. The following preferred specific embodiments are, therefore, to be construed as merely illustrative and not limitative of the remainder of the disclosure in any way whatsoever.

EXAMPLE 1
Composition of a Dragee in Each of the Stages

1st Stage (6 Dragees):
| | |
|---|---|
| 0.030 mg. | 17α-Ethinylestradiol |
| 0.050 mg. | d-Norgestrel |
| 33.170 mg. | Lactose |
| 18.000 mg. | Corn starch |
| 2.100 mg. | Polyvinylpyrrolidone |
| 1.650 mg. | Talc |
| 55.000 mg. | Total weight which is supplemented to about 90 mg. with a customary sugar mixture. |

2nd Stage (5 Dragees):
| | |
|---|---|
| 0.050 mg. | 17α-Ethinylestradiol |
| 0.050 mg. | d-Norgestrel |
| 33.150 mg. | Lactose |
| 18.000 mg. | Corn starch |
| 2.100 mg. | Polyvinylpyrrolidone |
| 1.650 mg. | Talc |
| 55.000 mg. | Total weight which is supplemented to about 90 mg. with a customary sugar mixture. |

3rd Stage (10 Dragees):
| | |
|---|---|
| 0.040 mg. | 17 α-Ethinylestradiol |
| 0.125 mg. | d-Norgestrel |
| 33.085 mg. | Lactose |
| 18.000 mg. | Corn starch |
| 2.100 mg. | Polyvinylpyrrolidone |
| 1.650 mg. | Talc |
| 55.000 mg. | Total weight which is supplemented to about 90 mg. with the usual sugar mixture. |

EXAMPLE 2
Composition of a Dragee for Each Stage

1st Stage (6 Dragees):
| | |
|---|---|
| 0.030 mg. | 17α-Ethinylestradiol |
| 0.050 mg. | d-Norgestrel |
| 33.070 mg. | Lactose |
| 18.000 mg. | Corn starch |
| 2.100 mg. | Polyvinylpyrrolidone |
| 1.650 mg. | Talc |
| 0.100 mg. | Magnesium stearate |
| 55.000 mg. | Total weight which is supplemented to about 90 mg. with the usual sugar mixture. |

2nd Stage (5 Dragees):
| | |
|---|---|
| 0.040 mg. | 17α-Ethyinylestradiol |
| 0.075 mg. | d-Norgestrel |
| 33.035 mg. | Lactose |
| 18.000 mg. | Corn starch |
| 2.100 mg. | Polyvinylpyrrolidone |
| 1.650 mg. | Talc |
| 0.100 mg. | Magnesium stearate |
| 55.000 mg. | Total weight which is supplemented to about 90 mg. with the usual sugar mixture. |

3rd Stage (10 Dragees):
| | |
|---|---|
| 0.030 mg. | 17α-Ethinylestradiol |
| 0.125 mg. | d-Norgestrel |
| 32.995 mg. | Lactose |
| 18.000 mg. | Corn starch |
| 2.100 mg. | Polyvinylpyrrolidone |
| 1.650 mg. | Talc |
| 0.100 mg. | Magnesium stearate |
| 55.000 mg. | Total weight which is supplemented to about 90 mg. with the usual sugar mixture. |

EXAMPLE 3
Composition of a Dragee for Each Stage

1st Stage (6 Dragees):
| | |
|---|---|
| 0.030 mg. | 17α-Ethinylestradiol |
| 0.050 mg. | d-Norgestrel |
| 33.070 mg. | Lactose |
| 18.000 mg. | Corn starch |
| 2.100 mg. | Polyvinylpyrrolidone |
| 1.650 mg. | Talc |
| 0.100 mg. | Magnesium stearate |
| 55.000 mg. | Total weight which is supplemented to about 90 mg. with the usual sugar mixture. |

2nd Stage (5 Dragees):
| | |
|---|---|
| 0.050 mg. | 17α-Ethinylestradiol |
| 0.075 mg. | d-Norgestrel |
| 33.025 mg. | Lactose |
| 18.000 mg. | Corn starch |
| 2.100 mg. | Polyvinylpyrrolidone |
| 1.650 mg. | Talc |
| 0.100 mg. | Magnesium stearate |
| 55.000 mg. | Total weight which is supplemented to about 90 mg. with the usual sugar mixture. |

3rd Stage (10 Dragees):
| | |
|---|---|
| 0.040 mg. | 17α-Ethinylestradiol |
| 0.125 mg. | d-Norgestrel |
| 32.985 mg. | Lactose |
| 18.000 mg. | Corn starch |
| 2.100 mg. | Polyvinylpyrrolidone |
| 1.650 mg. | Talc |
| 0.100 mg. | Magnesium stearate |
| 55.000 mg. | Total weight which is supplemented to about 90 mg. with the usual sugar mixture. |

EXAMPLE 4
Composition of a Dragee for Each Stage

1st Stage (6 Dragees):
| | |
|---|---|
| 0.050 mg. | 17α-Ethinylestradiol |
| 0.050 mg. | d-Norgestrel |
| 33.050 mg. | Lactose |
| 18.000 mg. | Corn starch |
| 2.100 mg. | Polyvinylpyrrolidone |
| 1.650 mg. | Talc |
| 0.100 mg. | Magnesium stearate |
| 55.000 mg. | Total weight which is supplemented to about 90 mg. with the usual sugar mixture. |

2nd Stage (5 Dragees):
| | |
|---|---|
| 0.050 mg. | 17α-Ethinylestradiol |
| 0.75 mg. | d-Norgestrel |
| 33.025 mg. | Lactose |
| 18.000 mg. | Corn starch |
| 2.100 mg. | Polyvinylpyrrolidone |
| 1.050 mg. | Talc |
| 0.100 mg. | Magnesium stearate |
| 55.000 mg. | Total weight which is supplemented to about 90 mg. with the usual sugar mixture. |

3rd Stage (10 Dragees):
| | |
|---|---|
| 0.050 mg. | 17α-Ethinylestradiol |
| 0.125 mg. | d-Norgestrel |
| 32.975 mg. | Lactose |
| 18.000 mg. | Corn starch |
| 2.100 mg. | Polyvinylpyrrolidone |
| 1.640 mg. | Talc |
| 0.100 mg. | Magnesium stearate |
| 55.000 mg. | Total weight which is supplemented to about 90 mg. with the usual sugar mixture. |

EXAMPLE 5
Composition of a Dragee per Stage

1st Stage (6 Dragees):
| | |
|---|---|
| 3.000 mg. | Estradiol valerate |
| 0.050 mg. | d-Norgestrel |
| 30.200 mg. | Lactose |
| 18.000 mg. | Corn starch |
| 2.100 mg. | Polyvinylpyrrolidone |
| 1.650 mg. | Talc |
| 55.000 mg. | Total weight which is supplemented to about 90 mg. with the usual sugar mixture. |

2nd Stage (5 Dragees):
| | |
|---|---|
| 5.000 mg. | Estradiol valerate |
| 0.050 mg. | d-Norgestrel |
| 28.200 mg. | Lactose |
| 18.000 mg. | Corn starch |
| 2.100 mg. | Polyvinylpyrrolidone |
| 1.650 mg. | Talc |
| 55.000 mg. | Total weight which is supplemented to about 90 mg. with the usual sugar mixture. |

3rd Stage (10 Dragees):
| | |
|---|---|
| 4.000 mg. | Estradiol valerate |
| 0.125 mg. | d-Norgestrel |
| 29.125 mg. | Lactose |
| 18.000 mg. | Corn starch |
| 2.100 mg. | Polyvinylpyrrolidone |
| 1.650 mg. | Talc |
| 55.000 mg. | Total weight which is supplemented to about 90 mg. with the usual sugar mixture. |

The preceding examples can be repeated with similar success by substituting the generically and specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A method of contraception which comprises administering for 21 successive days to a female of childbearing age a combination of an estrogen and a progestogen, for the first 4–6 days in a low but contraceptively effective daily dosage corresponding in estrogenic activity to 0.020–0.050 mg. of 17α-ethinylestradiol and in progestogenic activity to 0.050–0.125 mg. of d-norgestrel; for the next 4–6 days, at an estrogen daily dosage from 1–2 times the initial daily low dosage and at a progestogen daily dosage of from 1–1.5 times the dosage of the first 4–6 days; and for the next 9–11 days, at a daily estrogen dosage of from the initial daily dosage to the subsequent daily dosage and at a progestogen daily dosage higher than the previous daily dosages of up to 3 times that of the first daily dosage and corresponding in progestogenic activity to 0.100–0.250 mg. of d-norgestrel, followed by about 7 days without progestogen and estrogen administration.

2. A method according to claim 1 wherein the estrogen and progestogen are administered orally.

3. A method according to claim 1 wherein the estrogen and progestogen are administered in admixture.

4. A method according to claim 1 wherein the first combination of estrogen and progestogen is administered for 6 days, the second combination of estrogen and progestogen is administered for 5 days, the third combination of estrogen and progestogen is administered for 10 days and a placebo is administered for 7 days.

5. A method according to claim 1 wherein in at least one of the stages the estrogen is 17α-ethinylestradiol.

6. A method according to claim 5 wherein the estrogen in all three stages is 17α-ethinylestradiol.

7. A method according to claim 1 wherein in at least one of the stages the progestogen is d-norgestrel.

8. A method according to claim 7 wherein the progestogen in all three stages is d-norgestrel.

9. A method according to claim 1 wherein in at least one of the stages the progestogen is cyproterone acetate or 17α-ethinyl-19-nortestosterone acetate.

10. A method according to claim 1 wherein in all three stages the progestogen is d-norgestrel and the estrogen is 17α-ethinyl-19-nortestosterone acetate and they are administered orally in admixture.

11. A method according to claim 9 wherein 0.040 – 0.090 mg., 0.050 – 0.125 mg. and 0.100 – 0.250 mg., respectively, of d-norgestrel and 0.020 – 0.050 mg., 0.030 – 0.050 mg. and 0.025 – 0.050 mg., respectively, of 17α-ethinylestradiol are administered in the first, second and third stages.

12. The three-stage oral contraceptive composition comprising 21 separate dosage units, adapted for successive daily oral ingestion, consisting essentially of:
as the first stage, 4–6 dosage units containing, in admixture with a pharmaceutically acceptable carrier, a combination of an estrogen and a progestogen at low but contraceptively effective respective dosages corresponding in activity to 0.020–0.050 mg. of 17α-ethinyl-estradiol and in progestogenic activity to 0.050–0.125 mg. of d-norgestrel followed by, as the second stage, 4–6 dosage units containing, in admixture with a pharmaceutically acceptable carrier, a combination of an estrogen at a dosage from the same to twice the dosage of the first stage, and a progestogen at a dosage from 1–1.5 times the dosage of the first stage, followed by, as the third stage, 9–11 dosage units containing, in admixture with pharmaceutically acceptable carrier, a combination of an estrogen at a dosage from that of the first stage to that of the second stage, and a progestogen at a higher dosage than the first and second stages up to three times that of the first stage and corresponding in progestogenic activity to 0.100–0.250 mg. of d-norgestrel, optionally followed by, as the fourth stage, 7 dosage units free of estrogen and progestogen.

13. A composition according to claim 12 wherein the dosage units are in the form of tablets.

14. A composition according to claim 12 wherein in at least one of the stages the estrogen is 17α-ethinylestradiol.

15. A composition according to claim 14 wherein the estrogen in all three stages is 17α-ethinylestradiol.

16. A composition according to claim 12 wherein in at least one of the stages the progestogen is d-norgestrel.

17. A composition according to claim 16 wherein the progestogen in all three stages is d-norgestrel.

18. A composition according to claim 12 wherein in at least one of the stages the progestogen is cyproterone acetate or 17α-ethinyl-19-nortestosterone acetate.

19. A composition according to claim 12 wherein in all three stages the progestogen is d-norgestrel and the estrogen is 17α-ethinyl-19-nortestosterone acetate.

20. A composition according to claim 19 wherein 0.040 – 0.090 mg., 0.050 – 0.125 mg. and 0.100 – 0.250 mg., respectively, of d-norgestrel and 0.020 – 0.050 mg., 0.030 – 0.050 mg. and 0.025 – 0.050 mg., respectively, of 17α-ethinylestradiol and in the first, second and third stages.

* * * * *

UNITED STATES PATENT AND TRADEMARK OFFICE
CERTIFICATE OF CORRECTION

PATENT NO. : 3,957,982

DATED : May 18, 1976

INVENTOR(S) : Ursula Lachnit-Fixon and Alan G. Pitchford

It is certified that error appears in the above-identified patent and that said Letters Patent is hereby corrected as shown below:

In column 7, claim 1, line 7 and in column 8, claim 12, line 10, in each case, the numerical range "0.050-0.125" should read
-- 0.040-0.090 --.

In column 7, claim 10, line 43 and in column 8, claim 19, last line,
"19-nortestosterone acetate" should read -- estradiol --.

Signed and Sealed this

Seventeenth Day of August, 1993

Attest:

BRUCE LEHMAN

Attesting Officer

Commissioner of Patents and Trademarks